United States Patent
Wamsiedler

(10) Patent No.: US 6,176,903 B1
(45) Date of Patent: *Jan. 23, 2001

(54) DEVICE FOR REMOVING GASES FROM FLUIDS

(75) Inventor: Ralf Wamsiedler, Schonungen (DE)

(73) Assignee: Fresenius Medical Care Deutschland GmbH, Bad Homburg (DE)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/861,543

(22) Filed: May 22, 1997

(30) Foreign Application Priority Data

May 22, 1996 (DE) .............................. 196 20 591

(51) Int. Cl.⁷ .................................................. B01D 19/00
(52) U.S. Cl. ............................. 96/208; 96/209; 96/210; 96/212; 96/213; 210/436; 210/472
(58) Field of Search ............................. 96/208, 209, 210, 96/212, 213, 155; 210/436, 472; 95/261

(56) References Cited

U.S. PATENT DOCUMENTS

| | | | |
|---|---|---|---|
| 3,088,595 | * | 5/1963 | Robb ....................... 96/212 |
| 3,771,288 | * | 11/1973 | Wisman et al. ................. 96/210 |
| 3,827,561 |   | 8/1974 | Serfass et al. . |
| 3,920,556 |   | 11/1975 | Bowman . |
| 4,061,031 |   | 12/1977 | Grimsrud . |
| 4,279,626 | * | 7/1981 | Buchmiller et al. ................ 96/212 |
| 4,344,777 |   | 8/1982 | Siposs . |
| 4,368,118 |   | 1/1983 | Siposs . |
| 4,690,762 | * | 9/1987 | Katsura ..................... 96/212 |
| 4,860,591 | * | 8/1989 | Garland .................... 96/212 |
| 5,203,891 | * | 4/1993 | Lema ..................... 96/210 |
| 5,468,388 | * | 11/1995 | Goddard et al. ................ 96/155 |
| 5,622,545 | * | 4/1997 | Mazzei et al. ................. 96/212 |
| 5,849,065 | * | 12/1998 | Wojke ..................... 95/261 |

FOREIGN PATENT DOCUMENTS

| | | | |
|---|---|---|---|
| 32 15 003 |   | 4/1985 | (DE) . |
| 001212467 | * | 2/1986 | (SU) ..................... 96/210 |
| 001327909A1 | * | 8/1987 | (SU) ..................... 96/210 |
| 001699496A1 | * | 12/1991 | (SU) ..................... 96/210 |

* cited by examiner

*Primary Examiner*—Jay H. Woo
*Assistant Examiner*—Minh-Chau T. Pham
(74) *Attorney, Agent, or Firm*—Kenyon & Kenyon

(57) ABSTRACT

A device for removing gases from fluids, in particular from a dialyzing fluid, includes a container, which in the position of normal use is provided with a bottom first orifice and a bottom second orifice. Disposed inside the container is a partition wall which divides the container into a first chamber having the first orifice and a second chamber having the second orifice. The partition wall extends from the container bottom up to near the container cover, forming a gap-shaped interstitial space between the first and second chamber, and the container cover. Provision is made in the container cover for a venting orifice that is sealed by a hydrophobic filter. In one preferred embodiment, the first and second chamber form a tube-in-tube arrangement. The device according to the invention allows for a high separation rate to be achieved with a compact and simple design.

13 Claims, 2 Drawing Sheets

DEVICE FOR REMOVING GASES FROM FLUIDS

FIELD OF THE INVENTION

The invention relates to a device for removing gases from fluids, in particular from a dialyzing fluid.

BACKGROUND INFORMATION

When setting up an extracorporeal blood circuit, as well as when preparing dialyzing fluids for dialysis, a plurality of devices for separating out air are known, such as bubble traps or air-venting devices, whose task is to effectively separate out the gases, which are present and partly dissolved in the fluid from the fluid.

The dialyzing fluids used in dialysis release gases in response to low pressure air separators which usually include a laterally disposed upper inlet, whose intended use is to impress a helical path upon the inflowing fluid. In this context, the air bubbles are to be separated out through a hydrophobic filter situated at the top. An arrangement of this kind is disclosed, for example, by the German Patent No. 32 15 003. However, in practical use, it was determined that the suction created partly entrains the separated air into the outflow so that further precautions had to be taken to improve the separation. Thus, for example, separation aids in the form of small plates were introduced into the venting space. Furthermore, the air separators were often built with very long dimensions to form the largest possible separation surface.

A device is disclosed in U.S. Pat. No. 4,061,031 that can be used both as a flow meter as well as an air separator. The known device has a container, which is divided by a partition wall that includes two chambers, one chamber being provided with an inlet orifice, and the other chamber with an outlet orifice. The partition wall includes an opening, and extends from the bottom of the container up to near the container cover, forming a gap-shaped interstitial space between the inlet chamber and the outlet chamber as well as the container cover.

The cut-through partition wall is comprised of two plate-shaped elements in a staggered arrangement, the orifices of the inlet and outlet chambers being situated at the bottom of the container. Since the opening in the partition wall has a smaller cross-section than the inlet orifice, fluid columns of different heights form in the chambers, making it possible to measure the flow rate. In this context, the difference between the two fluid columns is a measure of the level of the flow rate.

In the known device, the two chambers function as bubble traps. The air bubbles entrapped in the fluid rise to the top of the chambers and remain as gas above the fluid level. An active separation is no longer possible when working with the known device. To keep the fluid from flowing over the top edge of the partition wall into the outlet chamber, the inlet chamber has an elongated shape, which leads to a relatively substantial overall height.

SUMMARY OF THE INVENTION

It is the underlying object of the invention to create a device for removing gases from fluids, which, with a compact and simple type of construction, will enable a high separation rate to be attained.

In the device according to the invention, the partition wall is formed as a continuous traversing body, so that the first orifice and the second orifice are in fluid communication only via a gap-shaped interstitial space. Furthermore, provision is made on the container cover for a venting orifice that is sealed by a vent unit, which permits gas to pass through, but not fluid. During operation, the container, i.e., the two chambers and the gap-shaped interstitial space, are completely filled with fluid. The is fluid to be degassed flows out of the one chamber, across the gap-shaped interstitial space beneath the container cover, into the other chamber. At the partition wall, a reversal of the flow direction takes place, the gases entrapped in the fluid are able to escape through the venting orifice provided on the container cover.

An especially high separation rate is achieved with a device of a compact design, particularly when the partition wall is conceived in the form of a hollow body, which, while forming the first and second chamber, is so arranged inside the container that the inner first chamber has a smaller cross-section than the outer second chamber. In this arrangement, the first chamber forms the inlet chamber and the second chamber the outlet chamber. Since the inlet chamber has a smaller cross-section than the outlet chamber, the flow rate in the first chamber and, thus, the static pressure acting on the venting orifice is increased. On the other hand, the dynamic pressure at the venting orifice is kept low, so that in spite of the increased flow rate in the first chamber, virtually no air is entrained.

In the device according to the invention, the vent unit can be designed, for example, as a hydrophobic membrane. This membrane is advantageously integrated in the container cover, so that the fluid to be degassed is pressed against the membrane. The hydrophobic membrane should form the largest possible working surface for the fluid and preferably extend nearly over the entire cross-sectional surface of the gap-shaped interstitial space.

In one preferred specific embodiment, provision is made for the influx of fluid to be able to take place horizontally into the first orifice to the first chamber, this horizontal influx of fluid advantageously provides a tangential flow component. As a result, the inflowing fluid is essentially carried upwards in a spiral shape, thereby improving the air separation. Thus, the inflowing fluid mixture is set into a rotational motion within the air separator according to the invention, through which means gas is automatically conveyed in the direction of the shared axis.

In another preferred specific embodiment, the bottom of the tubular inside part of the first chamber is elongated toward the lower end with respect to the bottom of the outside part of the second chamber and, accordingly, extends out downwardly. In this specific embodiment, the first orifice is arranged on the tubular side wall adjacent to the bottom and the intake connector is in fluid communication with the first orifice. Preferably, the connector is advantageously positioned tangentially to the partition wall.

Similarly, the outflow connector in fluid communication with the second orifice can likewise be arranged horizontally adjacent to the bottom of the container and open through into the second orifice. The outflow connector is preferably positioned tangentially to the container wall.

Especially preferred is the specific embodiment where the horizontal walls of the first chamber and of the second chamber are formed in an annular shape and, thus, constitute a tube-in-tube arrangement, so that a circular annular space is formed between the first chamber and the second chamber.

DETAILED DESCRIPTION

Figure 1:
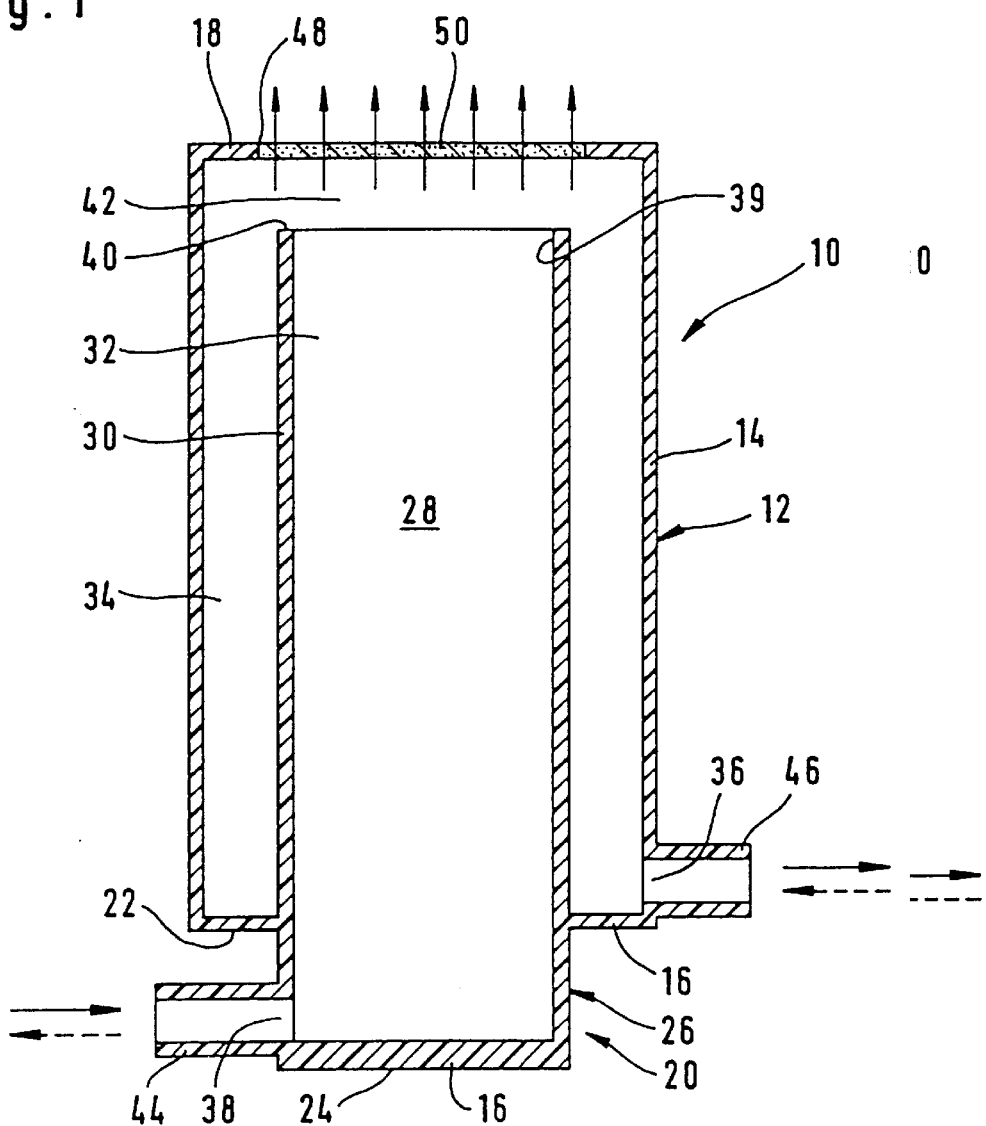
FIG. 1 shows a longitudinal section through a first embodiment of the device according to the present invention.

In FIG. 1, 10 denotes a device for removing gases from medical fluids, in particular for removing air from a dialyzing fluid, said device having a container 12. This container 12 has a substantially vertically arranged container wall 14, which is substantially circular in design in accordance with the specific embodiment shown in FIG. 1. Container 12 is delimited on its bottom side by a container bottom 16 and on its top side by a container cover 18.

In accordance with the specific embodiment shown in FIG. 1, container bottom 16 is offset, forming a step 20, through which means the container bottom is divided into an outer annular region 22 and an inner, substantially circular region 24. Therefore, stepped region 20 forms a substantially cylindrical region 26.

Container 12 has an inside space 28, which is divided by a toroidally-closed partition wall 30 into a first chamber 32, situated inside partition wall 30, and a second chamber 34, which has a substantially annular structure, surrounds partition wall 30 and is bounded by container wall 14.

Partition wall 30 is secured to container bottom 16 and is so formed in accordance with the specific embodiment shown in FIG. 1 that, at annular bottom region 22, it passes over into cylindrical region 26 and coincides with this region. On the other hand, however, the entire bottom 16 can also have a flat design, so that partition wall 30 stands on this bottom and is secured thereto.

In the area of bottom 16, provision is made in the area of first chamber 32 for a first orifice 38, which is advantageously conceived as an intake orifice. In accordance with the specific embodiment shown in FIG. 1, this first orifice 38 is positioned at downwardly projecting cylindrical region 26.

The end of partition wall 30 opposite bottom 16 is brought to the vicinity of the container cover and opens through there into a tubular orifice 39, which is defined by a circumferential tubular rim 40, functioning as a spillover weir for a supplied fluid. Provision is made between tubular rim 40 and container cover 18 for a gap-shaped flow space 42, which provides for flow communication between first chamber 32 and second chamber 34 over tubular rim 40.

The cross-sectional shape of container 12 as well as its container wall 14 and partition wall 30 is, for the most part, not critical. However, container 12, container wall 14 and partition wall 30 are preferably circular. Preferably, the two divided chambers formed from container wall 14 and partition wall 30 have a common circular center.

Inner first chamber 32 is advantageously constituted as an inlet chamber, while second chamber 34 lying concentrically to the outside functions as an outlet chamber. In this context, the outlet chamber advantageously has a larger cross-section than the inlet chamber, so that the fluid is able to flow substantially unhindered over tubular rim 40. In the container, as a whole, no significant pressure difference prevails.

It should also be added here, however, that the container may be designed for a different kind of incident flow, for example a flow from the outside to the inside, although this is not preferred.

Figure 2:
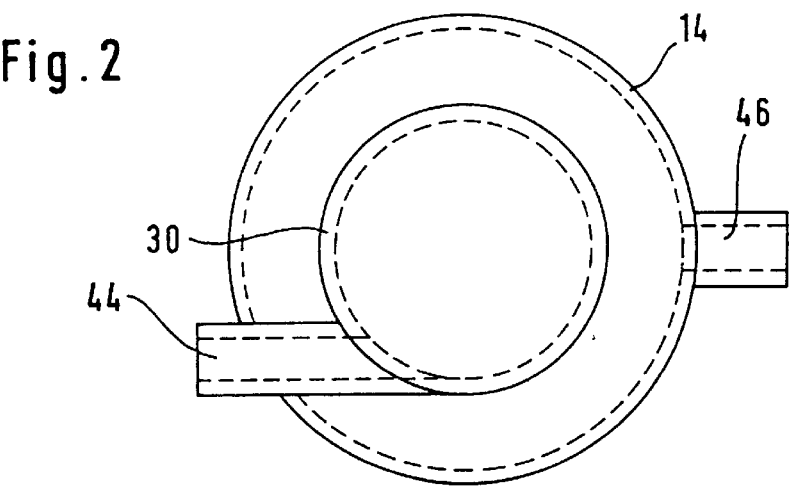
FIG. 2 shows a bottom view of the embodiment depicted in FIG. 1.

In accordance with the specific embodiment of FIGS. 1 and 2, a first tube connector 44 is arranged at first chamber 32 in the area of first tubular orifice 38. In this context, the longitudinal tubular axis of tube connector 44—as is apparent from FIG. 2 leads tangentially into the circular form of first chamber 32 and extends substantially horizontally in the position of normal use.

In addition, arranged at second chamber 34 in the area of second orifice 36 is a second tube connector 46, which functions as an outlet connector, its axis likewise being advantageously disposed horizontally in the position of normal use.

Figure 3:
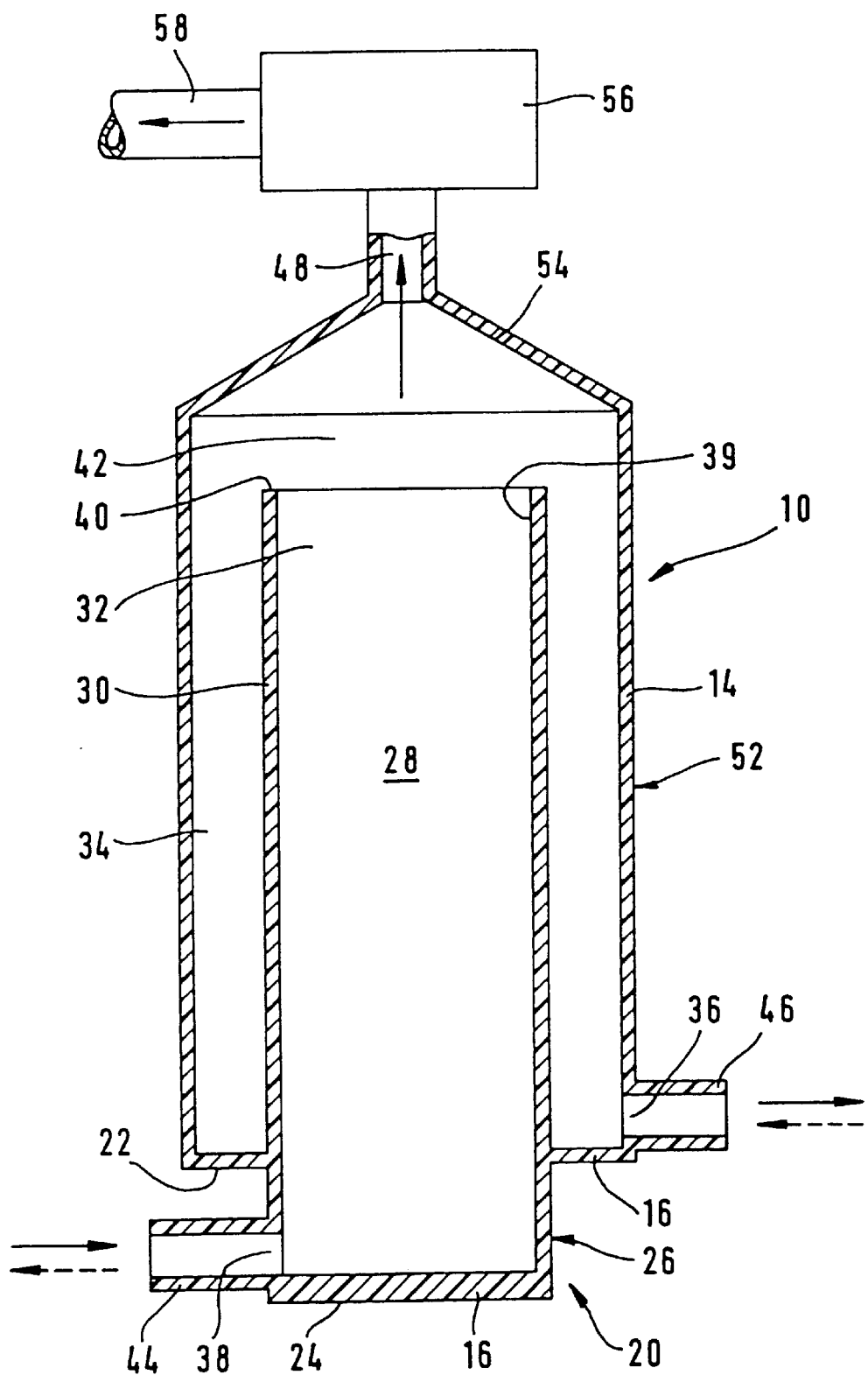
FIG. 3 shows a longitudinal section through a second embodiment of the device according to the present invention.

The arrows indicated at tube connectors 44 and 46 in FIG. 1 or 3 show the respective influx and effluence directions.

In addition, container cover 18 has a venting orifice 48, which is sealed by a vent unit. In the specific embodiment shown in FIG. 1, the vent unit is a microporous, hydrophobic filter 50, which allows the passage of the separated gas, but does not permit the passage of the aqueous fluid. To the extent that the hydrophobic filter is concerned, reference is made to the disclosure of German Patent No. 32 15 003.

Container 52 of FIG. 3, whose parts equivalent to those in FIG. 1 are labeled with the same reference symbols, differs from the specific embodiment shown in FIG. 1 merely in that container cover 54 is tapered conically toward the top in the direction of venting orifice 48 and in that venting orifice 48 has a boost pressure valve 56 as a vent unit, which is able to be connected via a line 58 to a hydraulic unit (not shown).

Containers 12 and 52 are usually made of a plastic material and function as primary air separators, for example, for separating out air in the preparation of dialyzing fluid. In this context, the air dissolved physically in the fluid is initially released from the freshly prepared fluid in a low pressure system. The fluid-air mixture is fed to tube connector 44, the mixture moving helically upwards because of the tangential introduction and, as a result, the air being automatically separated from the fluid in the direction of the body axis thereby forming small air bubbles.

The air separation follows then in the area of hydrophobic membrane 50, i.e., of boost pressure valve 56.

A considerable advantage of the device according to the invention for removing gases is the simple, continuous, very efficient separation of air, particularly when working with single-pass dialysis. A further advantage is that the container of the device is constantly filled with fluid, the result being very good disinfection or thorough flushing out of the system. Finally, because of its excellent separation properties, the device according to the invention can be reduced in size by about half as compared to air separators currently in use.

What is claimed is:

1. A device for removing gases from fluids comprising:
   a substantially cylindrical container having a side surface, a top end and a bottom end;
   a substantially cylindrical partition wall positioned in the container to divide the container into a first chamber, a second chamber, and an interstitial space substantially above the first and second chambers, wherein the first chamber is in fluid communication with the second chamber via the interstitial space;
   a cover positioned substantially at the top end of the container and including a hydrophobic membrane which permits passage of gas from the container while the container is completely filled with fluid such that the fluid is pressed against the hydrophobic membrane;

a first orifice formed on the partition wall adjacent to a bottom of the first chamber; and a second orifice formed on the side surface adjacent a bottom of the second chamber.

2. The device according to claim 1, wherein the partition wall extends from the bottom end of the container to substantially to the cover.

3. The device according to claim 2, wherein the diameter of the cross-section of the first chamber is smaller than the diameter of the cross-section of the second chamber.

4. The device according to claim 1, wherein a first connector is in fluid communication with a first orifice of the first chamber; a second connector is in fluid communication with a second orifice of the second chamber; and wherein the first connector and the second connector extend in opposite directions substantially horizontal to the first orifice and the second orifice.

5. The device according to claim 4, wherein the first connector is in fluid communication with the first orifice of the container and directs a rotational fluid flow into the first chamber.

6. The device according to claim 1, wherein the sealing member is a hydrophobic membrane.

7. The device according to claim 1, wherein the second chamber has an outlet orifice.

8. The device according to claim 1, wherein the partition wall is toroidally-closed.

9. The device according to claim 1, wherein the fluids are medical fluids.

10. The device according to claim 1, wherein the fluids are dialysis fluids.

11. The device according to claim 1, wherein the first chamber is in fluid connection with the second chamber only via the interstitial space.

12. A method for removing gases from fluids comprising the steps of:

passing fluid into a substantially cylindrical first chamber of a container, the container having a partition wall dividing the container into the first chamber, a second substantially cylindrical chamber and an interstitial space substantially above the first and second chambers, the fluid passing through a first orifice formed in the partition wall adjacent a bottom of the first chamber;

flowing the fluid from the first chamber over a top of the partition wall into the second chamber;

removing air from the fluid through a hydrophobic membrane positioned substantially at a top end of the container while the container is completely filled with fluid such that the fluid is pressed against the hydrophobic membrane; and passing the fluid out of the second chamber through a second orifice formed in a side surface of the container, adjacent a bottom of the second chamber.

13. The method as recited in claim 12 wherein the passing the fluid step creates a rotational fluid flow in the first chamber.

* * * * *